US008527291B1

(12) United States Patent
Kochendorfer

(10) Patent No.: US 8,527,291 B1
(45) Date of Patent: Sep. 3, 2013

(54) MEDICAL SEARCH ENGINE SYSTEM METHOD AND SOFTWARE PRODUCT

(75) Inventor: Karl Kochendorfer, Chicago, IL (US)

(73) Assignee: Medsocket LLC, Chicago, IL (US)

( * ) Notice: Subject to any disclaimer, the term of this patent is extended or adjusted under 35 U.S.C. 154(b) by 1064 days.

(21) Appl. No.: 10/634,252

(22) Filed: Aug. 4, 2003

Related U.S. Application Data

(60) Provisional application No. 60/400,872, filed on Aug. 2, 2002.

(51) Int. Cl.
*G06Q 50/00* (2012.01)

(52) U.S. Cl.
USPC .................................................. 705/2; 705/3

(58) Field of Classification Search
USPC .......................................................... 705/2, 3
See application file for complete search history.

(56) References Cited

U.S. PATENT DOCUMENTS

| | | | | |
|---|---|---|---|---|
| 5,966,126 A * | 10/1999 | Szabo | ............................. | 715/762 |
| 6,182,068 B1 * | 1/2001 | Culliss | ................................. | 707/5 |
| 6,199,077 B1 * | 3/2001 | Inala et al. | ..................... | 715/201 |
| 6,654,749 B1 * | 11/2003 | Nashed | ............................. | 707/10 |
| 2001/0037332 A1 | 11/2001 | Miller et al. | | |
| 2001/0051943 A1 * | 12/2001 | Drucker et al. | .................... | 707/3 |
| 2002/0078045 A1 * | 6/2002 | Dutta | ................................. | 707/7 |
| 2002/0169771 A1 * | 11/2002 | Melmon et al. | .................... | 707/5 |
| 2003/0130994 A1 * | 7/2003 | Singh et al. | ........................ | 707/3 |

OTHER PUBLICATIONS

The Ultimate Medical Information Finder. Website homepage: <http://www.mdchoice.com> (printed Jul. 21, 2003).
MD Consult: Clinical Information for Physicians. Website homepage: <http://www.mdconsult.com> (printed Jul. 21, 2003).
Medical Matrix. Website homepage: <http://www.medmatrix.org> (printed Jul. 21, 2003).
Medscape. Website homepage: <http://www.medscape.com> (printed Jul. 21, 2003).
Medical Library Association. Website homepage: <http://www.mlanet.org> (printed Jul. 21, 2003).
PrimeAnswers. Website homepage: <http://www.primeanswers.org> (printed Jul. 21, 2003).
Skolar MD. Website homepage: <http://www.skolar.com> (printed Jul. 21, 2003).
Webfeat. Website homepage: <http://www.webfeat.org> (printed Jul. 21, 2003).

* cited by examiner

*Primary Examiner* — Lena Najarian
(74) *Attorney, Agent, or Firm* — Barnes & Thornburg LLP

(57) ABSTRACT

A system, method, and computer software product for managing medical information on a networked computer system. An inputted search string is used with at least two medical sources accessible over a communications network. Results from the two or more sources are displayed in a single results page. Results can be ranked with special weight attributed to the source depending on source weighting criteria, the searcher's profile or healthcare worker type, or a combination of both of these factors. Results can be annotated and stored. Retrieval from storage is assisted by using keywords assigned to a particular document at the time of storage, or other similar metadata assigned to a particular document. Documents can have security designations assigned to them to limit read or read/write access to authorized users.

20 Claims, 9 Drawing Sheets

MEDICAL SEARCH ENGINE SYSTEM METHOD AND SOFTWARE PRODUCT

CROSS-REFERENCE TO RELATED APPLICATIONS

This application claims benefit of the U.S. Provisional Application Ser. No. 60/400,872, filed Aug. 2, 2002. The Provisional Application is incorporated herein by reference.

BACKGROUND

The present disclosure relates to a medical search engine and annotation system, method of use, and computer software product.

Physicians today are inundated with both administrative information and medical information as dramatic advancements in the field of medicine are made. Communication within a medical organization today is difficult to manage at best and managing an Intranet can be expensive. Physicians and all health care workers have a difficult time managing the enormous amount of information required to do their job. Physicians can no longer rely on their memory to practice the most effective medicine. On average, primary care physicians have two clinical questions for every three patients they see, but they do not have an effective and efficient tool to look for an answer to these questions. As an illustration of how well this problem is known in the art, there is an old saying that half of what a doctor learns during medical training is outdated in five years. Because of this problem, there is a need for an information retrieval tool that can be integrated into the workflow of doctors in their practices, students in their training, and other healthcare personnel in the field.

Electronic sources of medical information are available. Such medical sources include Internet-based or other communications network-based web sites at which a user can request and retrieve medical information. Often these medical sources are directed to particular category of medical literature, for example, one source may focus on textbook text, others on journals, other on drug information, and still others practice guidelines for physicians and other health workers. It is desirable to be able to access one or more of these medical sources simultaneously so that a multi-disciplinary search can be performed. Searching such sources individually can be time consuming and bear considerable administrative overhead because each source may require entering into a separate licensing agreement and management of a separate set of access rights such as user licenses, user names, and passwords, and payment option. It is desirable to have a system, method, and/or computer program product that manages the disparate access rights, licenses, and payments in one simple interface.

Further, along with searching and managing medical resources, doctors and other users need a system that allows annotation and intelligent retrieval of information found using the system. It is desirable to have a system, method and computer program product that allows a user to assign retrieval or indexing related information, often referred to as metadata, to found search results, for more manageable and efficient information retrieval.

SUMMARY

The present disclosure provides a system, method, and computer software product for managing medical information on a networked computer system, such as a computer system connected to the Internet or a corporate Intranet. The method consists of providing a user with a search interface into which a search string can be inputted, and performing a search using the search string by accessing at least two medical sources to produce a set of search results. The two sources are electronically accessible via a communications network such as the Internet. The search results are then displayed in a categorized browseable format.

The search results can be sorted depending on a profile of the healthcare worker that performs the search. Further, these results can also be formatted or ranked according to source weighting criteria.

The present system, method, and computer program product can be used to automatically log into medical sources where an authentication identifier, such as a user name and password, is required.

Found search results can be stored for later retrieval which may involve assigning a keyword or other metadata to that search result, storing a particular result as favorite, or moving the result to a browseable folder. Stored results and personal documents can be assigned a user access parameter corresponding to a desired level of access for other users.

Additional features will become apparent to those skilled in the art upon consideration of the following detailed description and drawings exemplifying one or more embodiments as presently perceived.

BRIEF DESCRIPTION OF THE DRAWINGS

The detailed description particularly refers to the accompanying figures in which.

DETAILED DESCRIPTION

Figure 1:
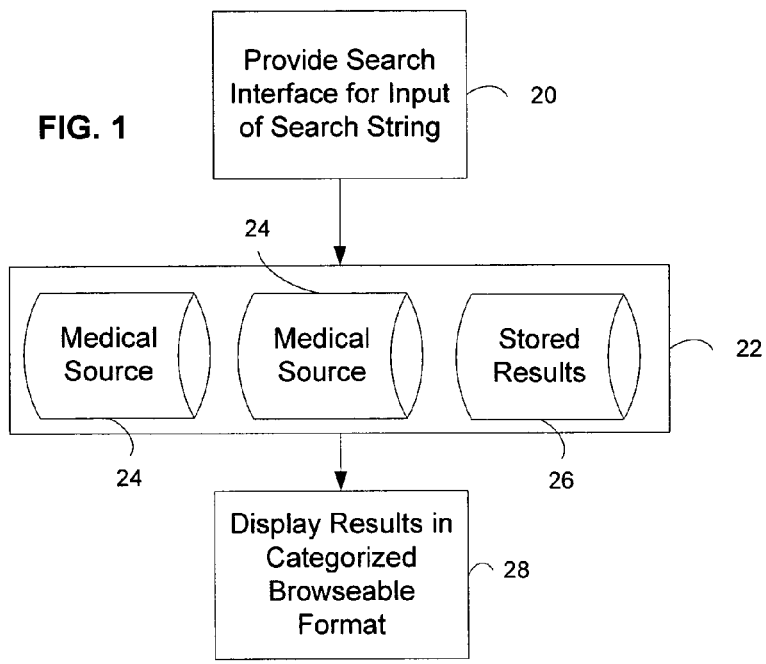
FIG. 1 is a simplified diagrammatic view of steps of the current method of managing medical information.

While the present disclosure may be susceptible to embodiment in different forms, there is shown in the drawings, and herein will be described in detail, embodiments with the understanding that the present description is to be considered an exemplification of the principles of the disclosure and is not intended to limit the disclosure to the details of construction and the arrangements of components set forth in the following description or illustrated in the drawings.

The present system, method, and computer software product is intended for use in a medical facility including but not limited to hospitals, medical organizations, clinics, etc. Individual users can be any type of healthcare worker including but not limited to general practice physicians, specialty physicians, researchers, medical students, nurse practitioners, insurance company employees, hospital administrators, and others involved with medical records, medical research, patient care, or the medical field in general. For simplicity, these categories of person are collectively referred to as "healthcare workers" or "users."

Healthcare workers require various types of medical or healthcare related information (collectively, "medical information"), such as information about a particular disease, effects of a particular drug, treatments, and so forth. Often different types of medical information references provide information on the various types of medical information from different perspectives or with a different focus. For example, a medical textbook may report an established diagnosis and tested treatment, while a journal may report recent or cutting edge findings. For simplicity, all sources of electronic medical information are referred to hereinafter as "medical sources."

The current system, method, and computer program product provide for searching of at least two medical sources over a communications network. A communications network can be a publicly available network such as the Internet or World Wide Web, but can also be part of a company intranet, a network connecting hospitals, a network connecting research or educational facilities or combinations thereof. Searches are performed using a search interface on a graphical user interface communicating with the communications network, such as the graphical user interface provided by a commercially available web browser.

As shown in FIG. 1, the method of the current disclosure includes a number of steps to perform a search across multiple medical sources. In a first step 20, a user is provided with a search interface for input of a search string. A search string can be a word or phrase that is desired to be compared against medical information documents. The search string can also contain wildcards and Boolean search protocols for more advanced searching. The search interface can be programmed using standard HTML programming language, or may be linked directly to a web server software module (See FIG. 8) to be discussed in more detail below, in which case the search interface may be programmed by any software language including but not limited to C#, Java, Visual Basic, or coded from web site authoring suites such as Cold Fusion, Visual Basic Studio, or Visual Studio.NET.

In a second step 22, the inputted search string is used to query at least two medical sources 24 across a communications network. The medical sources 24 are electronically accessible. Many web-based medical sources 24 provide their information at no-cost and can therefore be screen scraped, i.e. have the information produced by their web site copied for transmittal to the user. Alternatively, many web sites allow integration using Web Services to allow their content to be searched and/or copied. In addition, other medical sources 24 provide some Application Programming Interface (API) and/or screen scraping to allow seamless access to information found therein. The current system, method, and computer program product is able to communicate and retrieve information from any of these types of medical sources 24.

Such communication with medical sources also allows generally for real time display of results. Real time display of results means that results are displayed in the same session that the user is performing the search. Generally, results from disparate medical sources can be displayed in under 2 minutes, although longer durations may be needed if a search is complex, many documents are found, network congestion exists, a medical source 24 is malfunctioning, or for other reasons. As shown in FIG. 1, stored results 26 that were found in previous searches can be queried along with medical sources 24 as well as searching personal documents 25, shared intranet documents, and other documents in an intranet when an intranet or combination intranet/Internet embodiment of the current system, method, or computer software product is being used.

It should be noted that the search interface can utilize a world wide web interface usable with common web browsers such as Microsoft Explorer or Netscape Navigator. Browsers modified for handheld devices and personal digital assistants like the Palm Pilot, or similar portal devices, including devices running Windows Pocket Internet Explorer may also interact with the search interface.

The final step 28 is having the results of the search, displayed to the user on the search interface. This display allows a user to browse through the search results using their browser and to select or "click" a particular search result to read it, save it, or print it.

Figure 2:
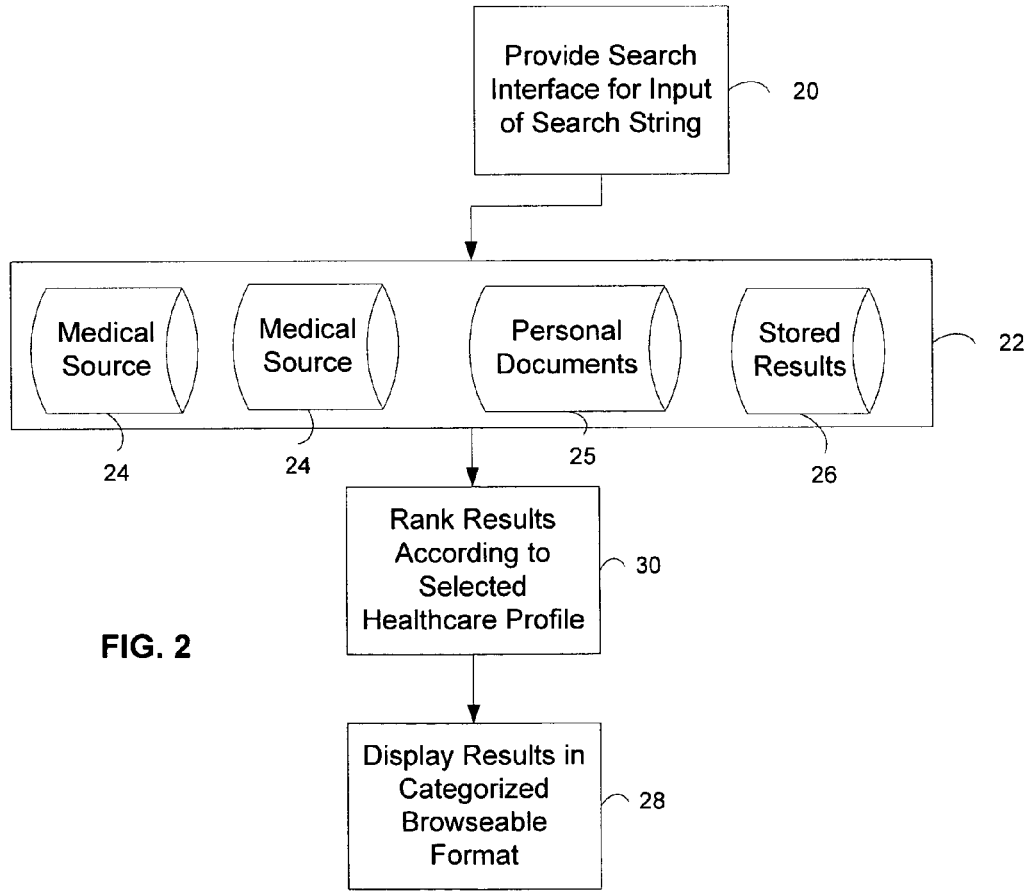
FIG. 2 is an alternative embodiment of the method of FIG. 1 in which search results are ranked according to a selected healthcare profile.
Figure 12:
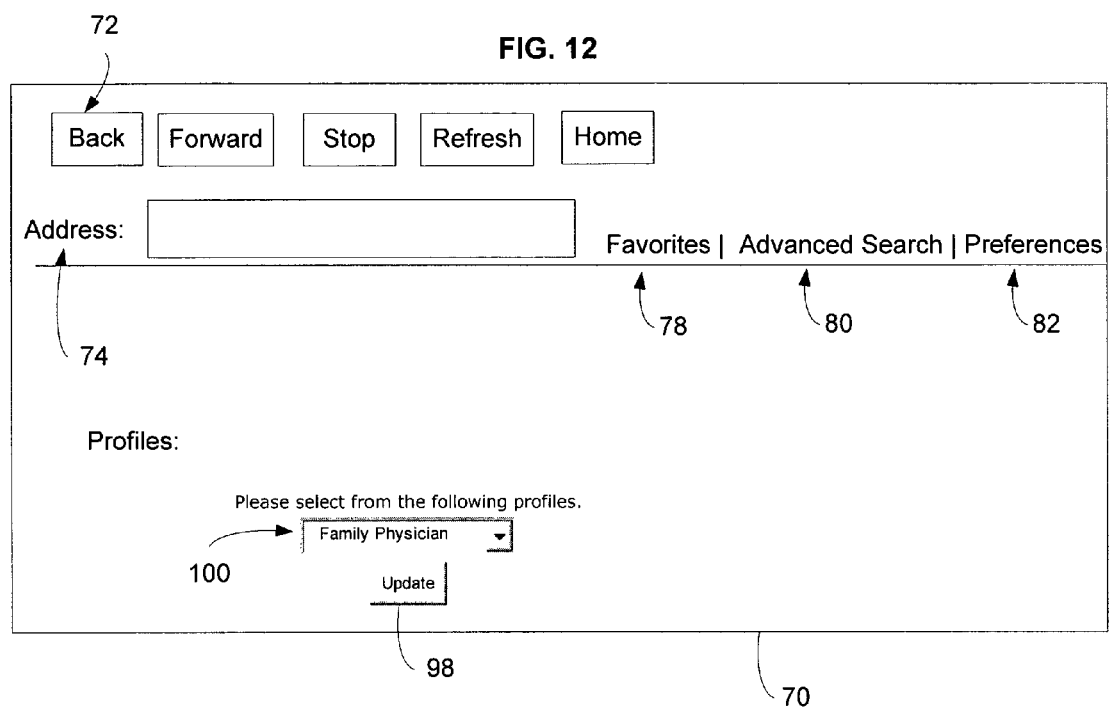
FIG. 12 is a representation of a web browser screen display showing a profile section drop down menu box.

As shown in FIG. 2, the current method may add an additional step 30 before the results are displayed, step 30 involves ranking the results prior to display. The results can be ranked depending on the type of healthcare worker performing the search. This is accomplished by weighting results from medical sources 24 preferred or more relevant to a particular type of user higher up on the search results list. This weighting improves the likelihood that the most important and useful information to that user will be displayed first. A user type is hereinafter referred to as a user "profile" which represents the source weighting parameters for that particular type of user. An example of a web screen for selecting a user profile is shown in FIG. 12 and discussed in more detail below.

Figure 3:
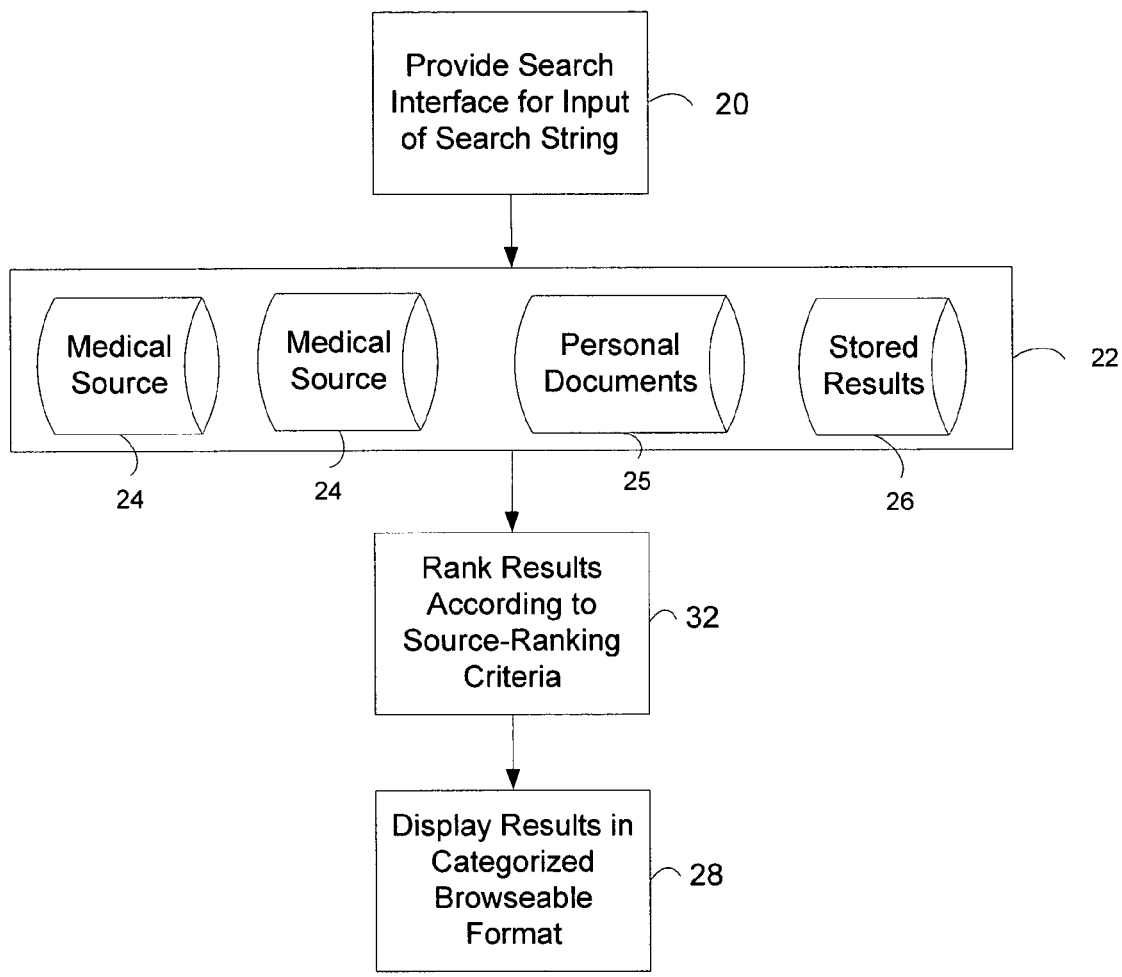
FIG. 3 is another embodiment of the method of FIG. 1 in which the search results are ranked according to source weighting criteria.
Figure 11:
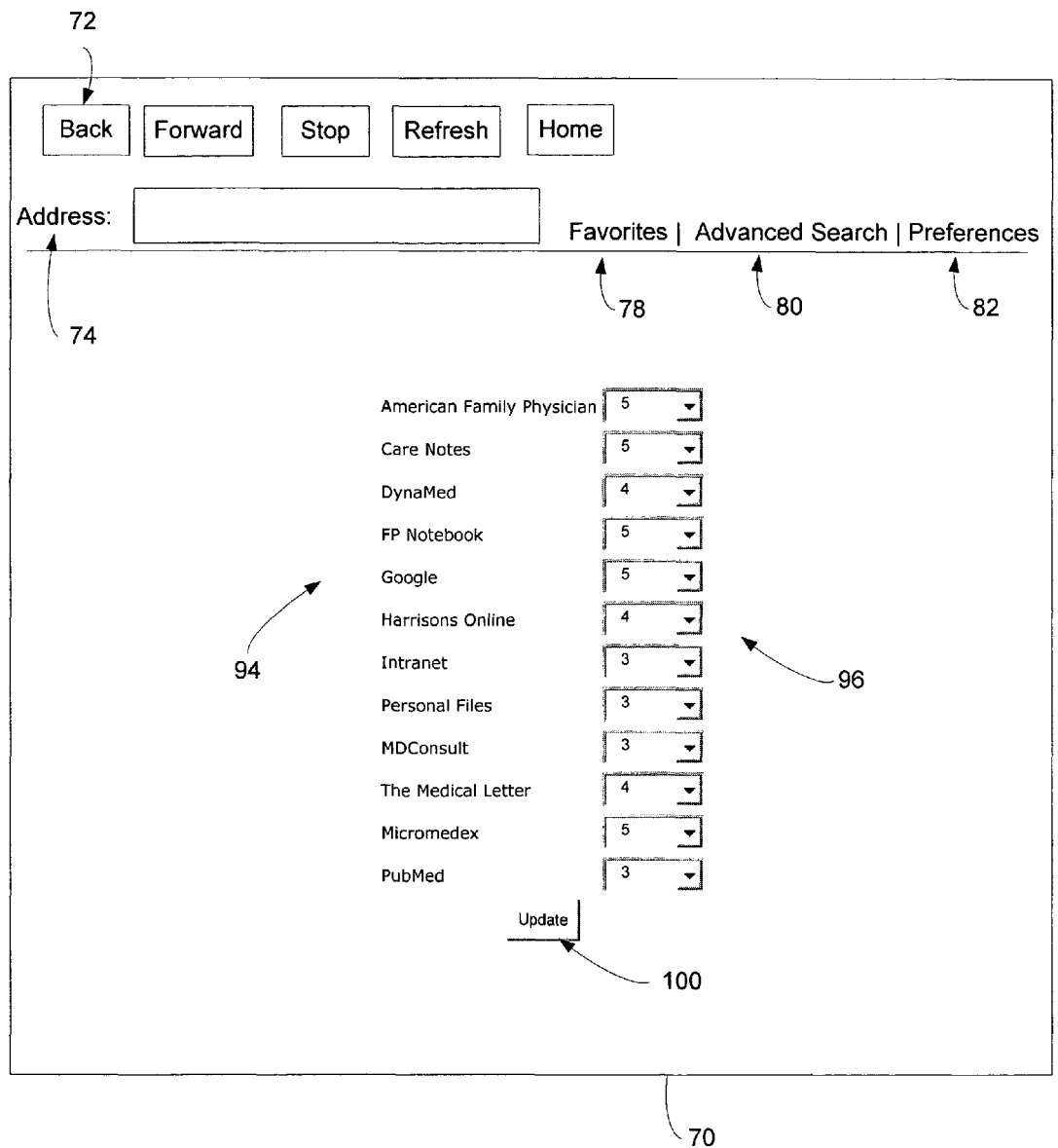
FIG. 11 is a representation of a web browser screen display showing a preferences web page in which source weighting criteria can be assigned to one or more sources.

As shown in FIG. 3, in an alternative embodiment, an intermediate step 32 between querying the medical sources 24 and stored results 26 and the step of displaying the results to the user 28 is to rank the results according to source-ranking criteria. This ranking is automatically performed based on the user type in the previous embodiment of FIG. 2. In this embodiment, the user is able to rank each source individually to produce a customized ranking order. An example of screen display showing in which source are assigned ranking is shown in FIG. 11 to be discussed in more detail below.

Figure 4:
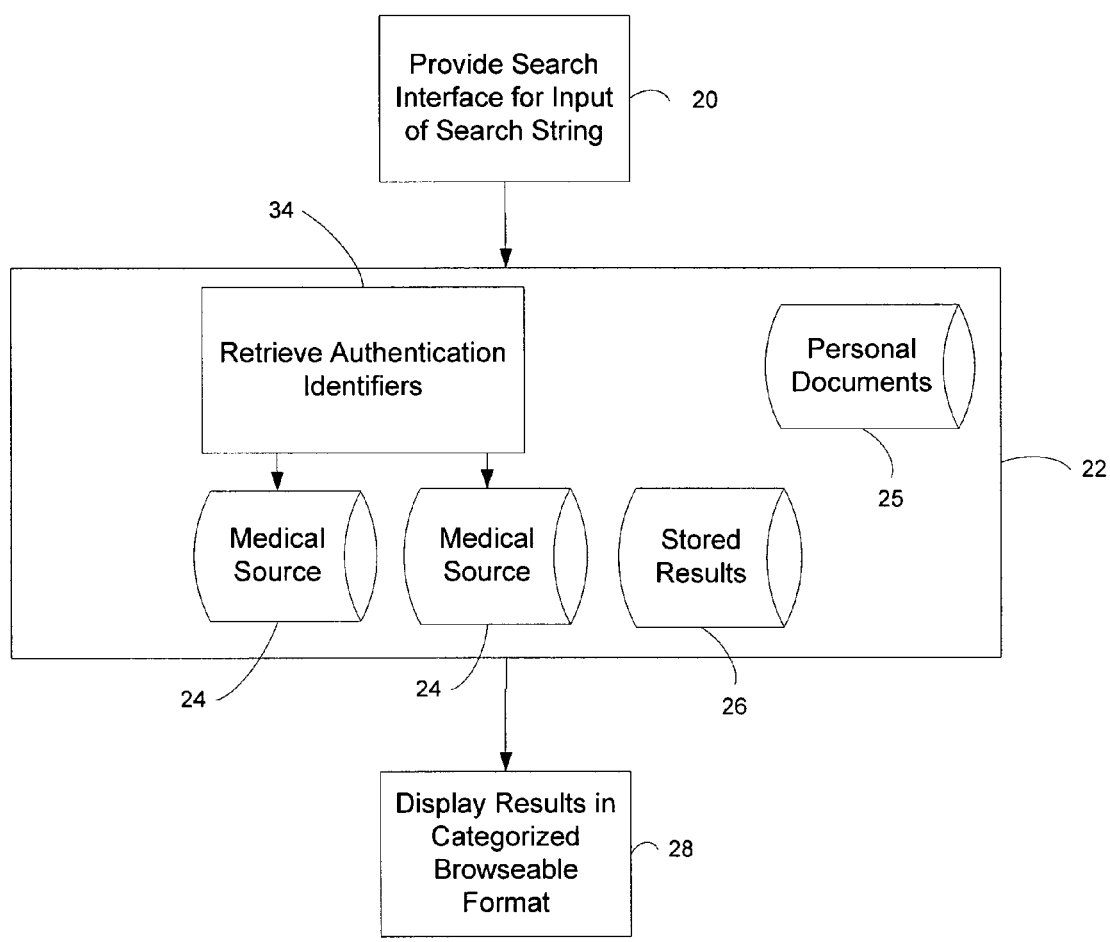
FIG. 4 is another embodiment of the method of FIG. 1 in which the authentication identifiers used for accessing medical sources are retrieved to enable access to those medical sources.

Referring now to FIG. 4, certain medical sources 24 do not allow free access to their documents or otherwise do not allow access without some user identification or authentication. For example, many medical source web sites may require the user to login using an assigned user name and password. The current method allows a user to store their user name or password, or provides means for accessing the information on the third-party medical source's server without entering a password. Thus authentication identifiers, such as a user name and password, is retrieved in a step 34 before the medical sources 24 are queried. In this manner, a user can search multiple sources simultaneously, regardless of whether the sources require logging in or authentication, directly from the current method, system, or computer software product's search interface. In addition, the user can be presented with an option to sign-up for or purchase access to a particular medical source while using the search interface. This may or may not require the user to be given or select an authentication identifier such as a new username and/or password. Thus medical sources and their associated authentication identifiers can be added and managed easily from the search interface.

Figure 5:
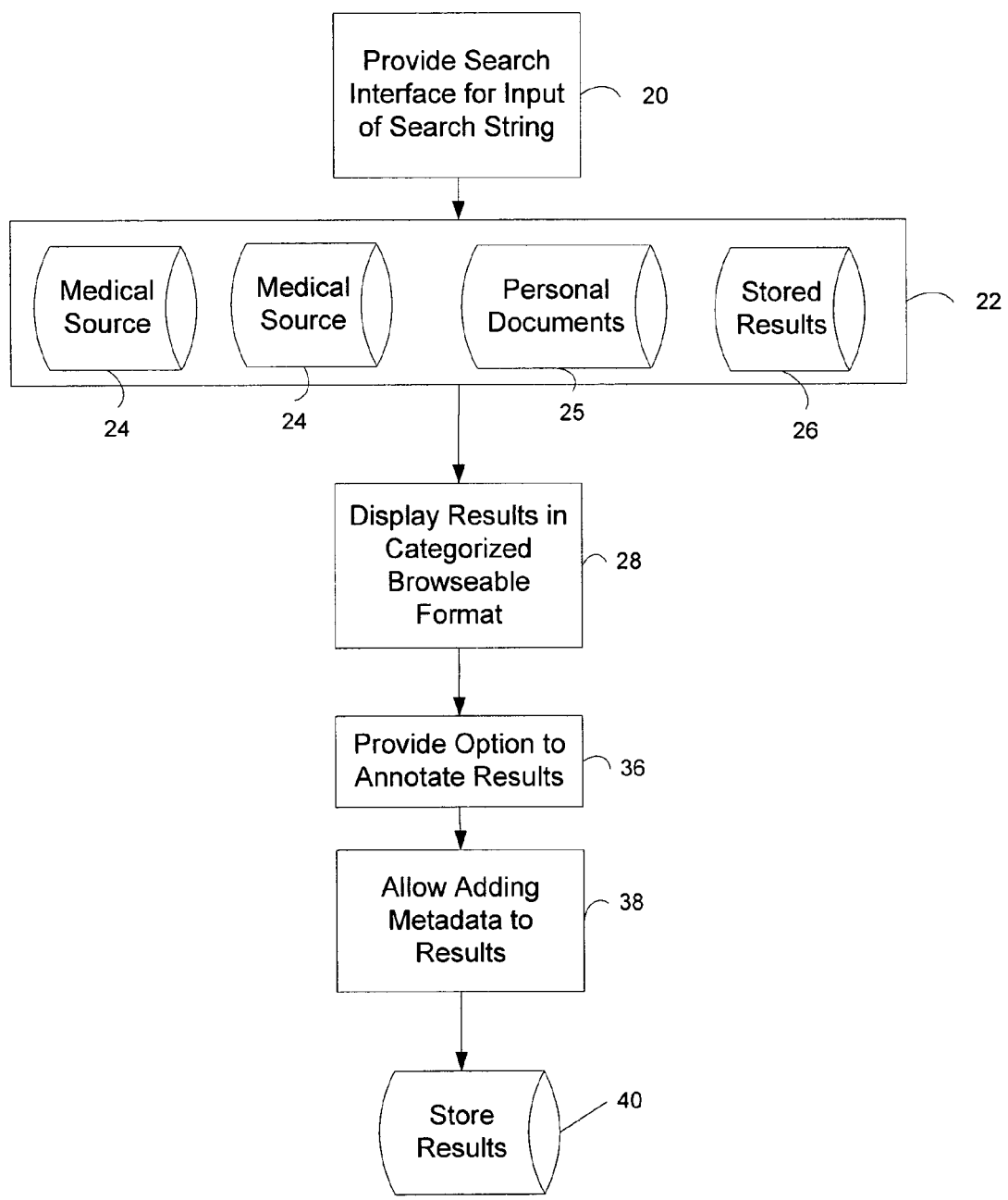
FIG. 5 is another embodiment of the method of FIG. 1, wherein the method has the additional steps of annotating documents found by the search and adding retrieval information to those results to assist with later retrieval.

As shown in FIG. 5, after the step 28 of displaying the search results to the user, an optional next step 36 of the current method is to allow the user to annotate, or mark-up documents found during the search. The ability to annotate documents digitally is useful because it eliminates the need for paper and helps expedite paperless office goals. Digital annotation schemes may include but are not limited to marking up, highlighting, underlining, drawings, and making notes on the electronic documents. Annotations may be stored on the system in variety of formats such as, for example, XML or GIF images. Annotation files are retrieved along with the source documents when the source documents are requested.

The ability to annotate a document can also be supplemented when an alternative embodiment of the current method adds a step 38 that also allows a user to add information about the document so that the document can later be retrieved by entering that information. Such information is referred to as metadata and can be as simple as assigning a keyword, or be more sophisticated such as by entering information into client-specific or disease-specific fields or fields related to other information that is stored with the document. The document can later be retrieved by entering matching metadata into search queries. In a final step 40, the resultant document along with its metadata is stored for later retrieval.

Additionally, stored documents can have user access parameters assigned to them. User access parameters can serve several functions. One function is to limit those who can access a document (i.e. that have "read access"). Similarly, a particular user or group of users can be given different combinations of read access or read/write access. Access can be granted to other selected users based on their information such as their position in the healthcare organization or based on which login and password that user uses. For example a physician or medical school professor may have read/write access while nurses or medical students would have limited read access. Other embodiments of authentication schemes beyond passwords, such as biometric devices or pass-cards may be used as well.

A second function of user access parameters is to ensure that, in an embodiment in which the medical sources 24 have user restriction or licensing requirements, that such restrictions and requirements are respected. For example, a medical source 24 may provide unlimited uses by physicians but not by nurses. The system can recognize the user's status from their login and provide access only to those sources that grant licenses to a corresponding class of users.

A third function of user access parameters is to authenticate the user for Continuing Medical Education credit. Many states require physicians to regularly take a certain number of accredited hours of medical education each year. The current method, system, and computer software product provides a convenient interface for viewing or participating in Continuing Medical Education programs. Such program typically require some assurances that the user is actually the physician requesting credit. The user access parameters can be used to authenticate the user and therefore provide the necessary assurances. Further, physicians utilizing the method, system, and computer software product can receive CME credit for looking up answers to questions as part of their day-to-day job.

Figure 6:
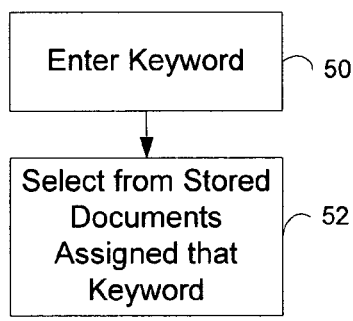
FIG. 6 is a simplified diagrammatic view of steps to retrieve a document stored on the system using a keyword.
Figure 7:
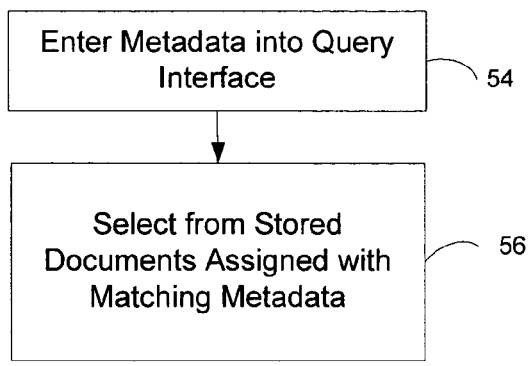
FIG. 7 is a simplified diagrammatic view of the steps to retrieve a document stored on the system using metadata information as the query.

FIGS. 6-7 show two embodiments of steps to retrieve the stored documents. In a first step 50, a user can input a keyword to retrieve a list of all stored documents having that keyword assigned to them. The user can in a second step 52, select from the list of documents matching that keyword to review, edit, print, or otherwise manipulate the selected document.

Alternatively, as shown in FIG. 7, the user can take the step 54 of entering other search information into search query fields. This information is then compared against the metadata for each document. Matching document are retrieved in a subsequent step 56. In this manner, documents can be indexed for convenient and efficient retrieval.

Figure 8:
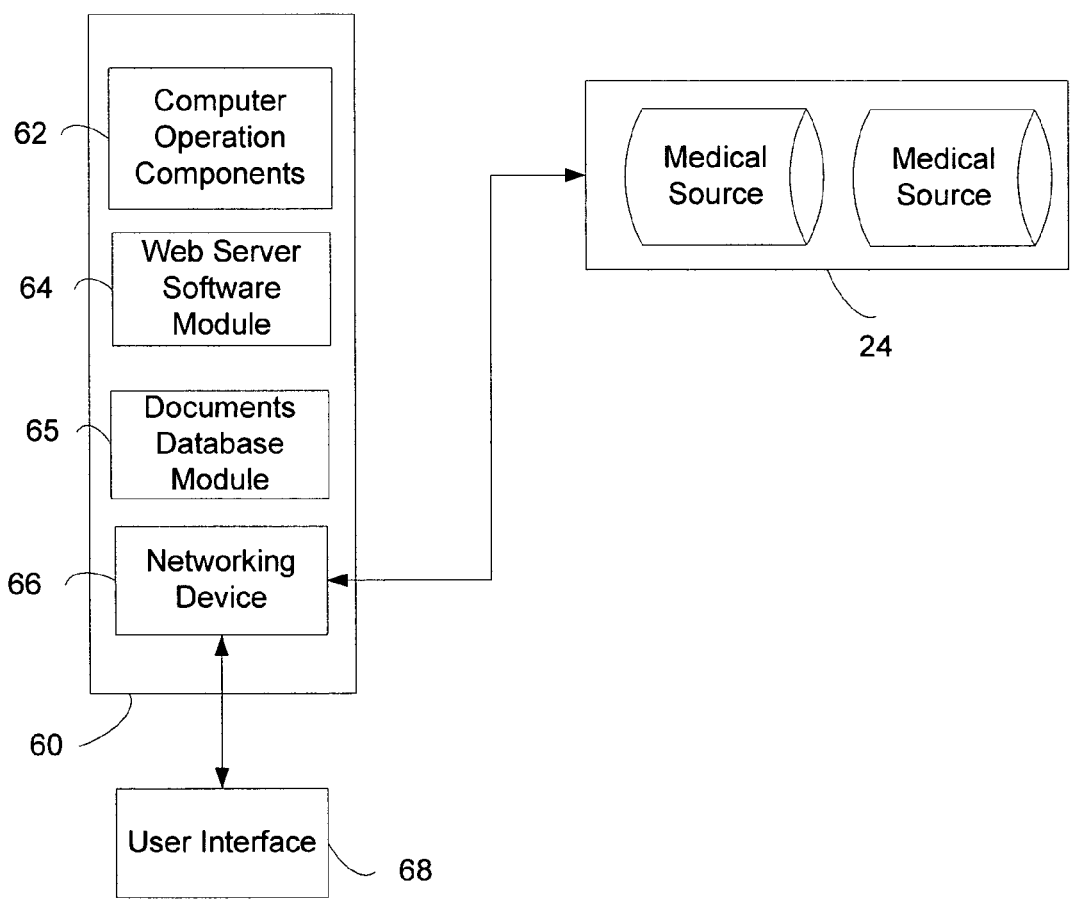
FIG. 8 is a simplified diagrammatic view of a system for managing medical information including a host system, user interface on a user's system, and one or more external medical sources.

FIG. 8 shows a simplified diagrammatic view of a host system 60 for managing medical information. The system 60 includes computer operation components 62 that are generally found in industry standard general purpose computers and/or server systems, such as a processor, motherboard, and storage device. The storage device may be a hard drive, a tape drives or the like, or combinations of multiple hard drives or tape drives for security and system failure redundancy purposes such as RAID arrays. The storage device has software loaded thereon for operating the computer operation components 62 as well as storing the web server software module 64. The term "software module" referenced in this disclosure is meant to broadly cover various types of software code including but not limited to routines, functions, objects, libraries, classes, members, packages, procedures, methods, or lines of code together performing similar functionality to these types of coding used to enable a processor to perform tasks specified by the module.

The web server software module 64 may be written in any web server authoring software language. The server allows access by users via a well known user interface 68, such as a browser interface, available on a user's workstation, desktop computer, or handheld device. The system 60 also includes a documents database module 65, stored on the storage device of the system 60, which stores and organizes stored search results, and other files used by the system 60. The documents database module 65 may utilize any software programming language or customized commercially available database product such as Microsoft SQL Server.

The system 60 also includes a networking device 66 such as an Ethernet network card for connection to the user interface 68 and the medical source or medical sources 24 via a communications network such as the Internet or a private virtual network.

Figure 9:
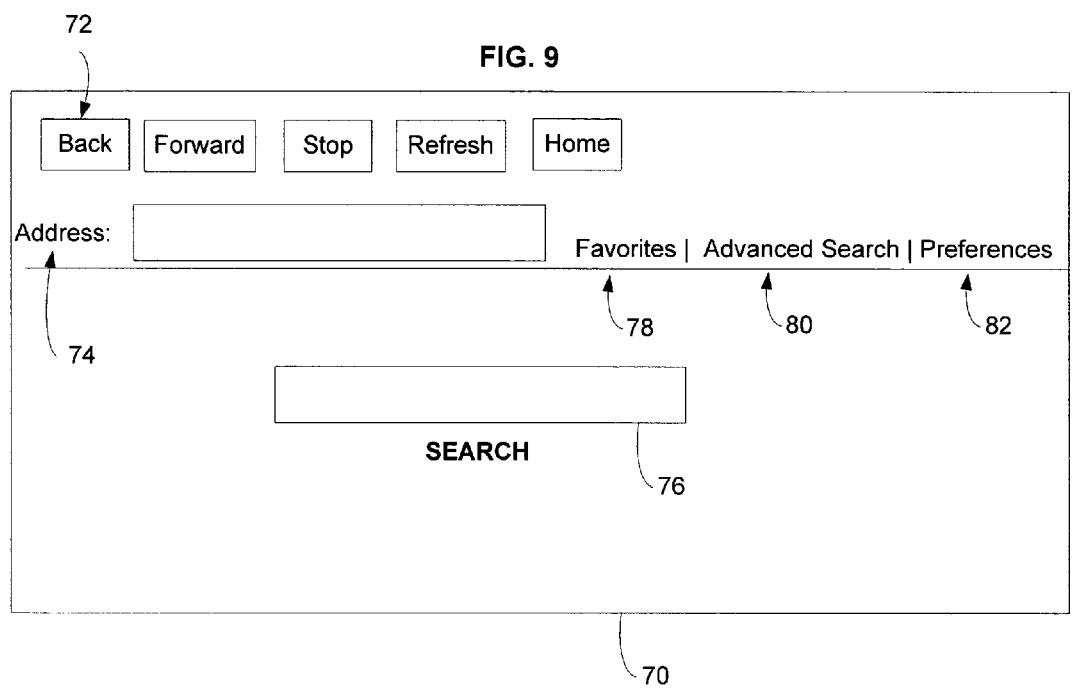
FIG. 9 is a representation of a web browser screen display showing a search interface.

FIG. 9 shows one embodiment of a web site interface 70 embodiment of the user interface 68. The web site interface typically includes browser controls 72 such as a back button, forward button, stop button, refresh button, and return to home button. The web site interface 70 further includes an address bar 74 into which a user can input the URL to connect to the system 60. Controls 72 and address bar 74 are typically functions of the user's browser setting so they may be shown, hidden, or have additional or fewer buttons depending on the user's browser's selected customization settings.

The initial screen of interface 70 also includes a search box 76 into which the user can enter a search term. A favorites link 78, advanced search link 80, and preferences link 82 are also provided and can be activated when a user clicks on a particular link. As described above, the favorites can be stored documents that user would like to keep readily available for retrieval. Documents are stored in the favorites section in a personal notes folder interface which is a hierarchical folder system commonly known in the art, and can be browsed by clicking through folders and then clicking a desired stored document.

The advanced search link 80 directs the user to a more elaborate search interface in which the user can enter additional or alternative search criteria beyond a simple search string. Examples may include selecting particular sources in which to search, selecting a date range, or being able to use wildcards and Boolean connectors to limit or more finely define parameters for the search.

Figure 10:
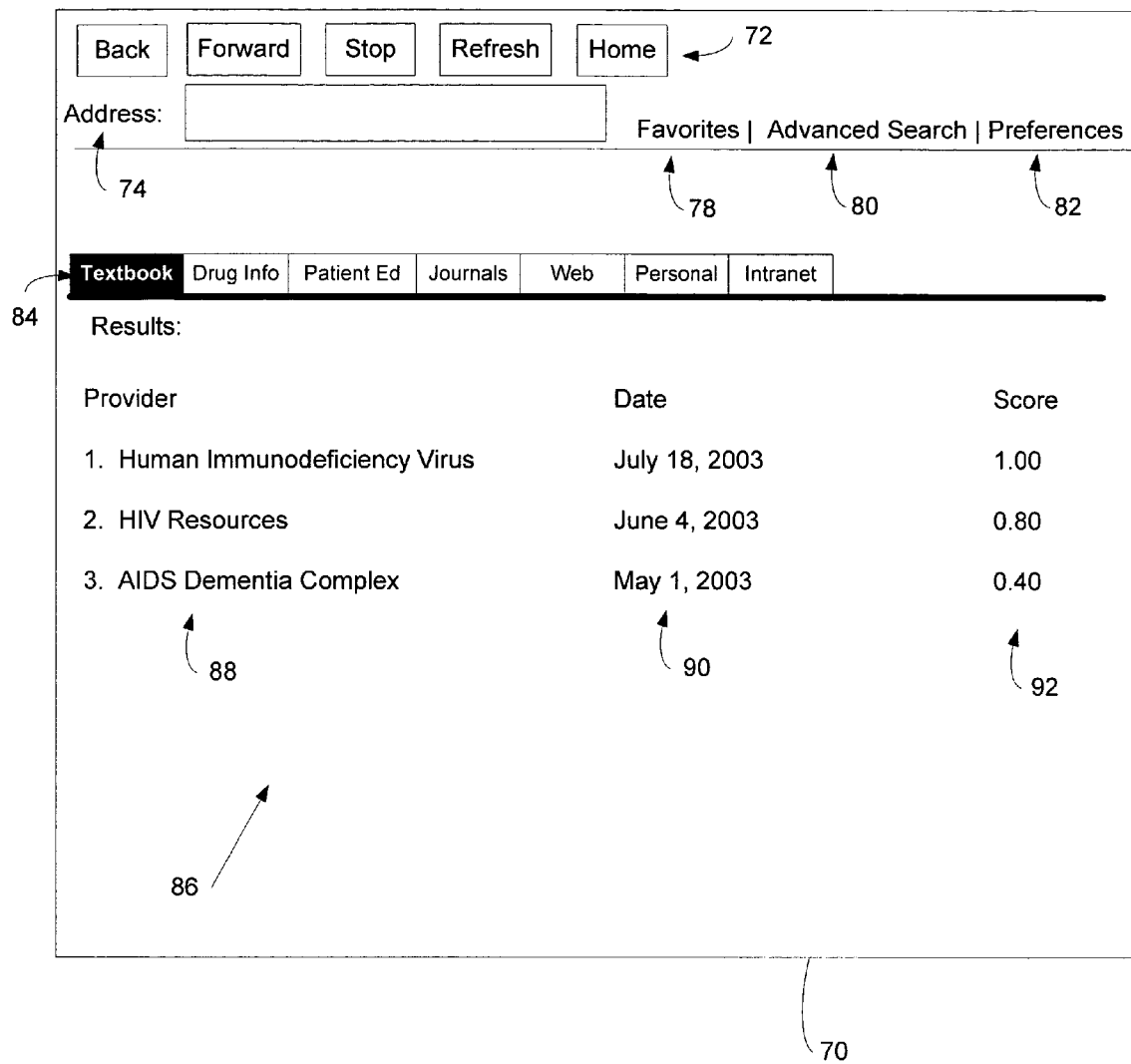
FIG. 10 is a representation of a web browser screen display showing a search results web page including category selection tabs across a top section of a search results area.

FIG. 10 is an example of one embodiment of the search results screen for a search run on the search string "AIDS." Search results are grouped in one more category tabs 84. Example tabs for the textbook, drug information, patient education, journal, web, personal notes, and intranet documents categories are shown. Other categories can include Differential Diagnosis, Evidence Based Medicine (EBM) Resources, Atlases, Images, Medical News, Discussion Forums, Guidelines, and Tools such as, for example, medical calculators. The categories are "browseable" because a user can click a desired tab and view its corresponding search results. Also, users can customize their tabs to configure which tabs are displayed, the tab order, position on the screen and so forth.

The searched results can be displayed in a number of different embodiments. One example, shown in FIG. 10, positions three columns in the search results area 86. The first provider column 88 includes a listing of the references and can also include the name of the medical source from which each reference is retrieved (not shown). The search results may be formatted to consolidate multiple search results from a common medical source into a single search result link. In such an embodiment, a user is able to first scan over the links from all found medical sources and then click a desired consolidated link to find more specific page or article references within the selected medical source. The second date column 90 shows the date of publication of the reference, and the third score column 92 shows the relevancy score. Although a one-point relevancy score is shown, other scoring methods such as 100 point scale, a number of graphical icons such as in the shape of stars, or a letter grade may be used as well.

Although various methodologies for ranking the search can be used, the following is one methodology. The ranking algorithm is applied to each tab category (e.g., textbook, journal) separately to create a ranked list for each category. The rankings are based in part on how the medical sources 24 report their relevancies. Medical sources differ in how results and/or relevancy scores are reported. Some medical sources 24 report their results and assign a relevancy score to each result. Other medical sources 24 report their results in a ranked order but do not actually assign a score.

For those sources that assign a relevancy score, these scores are normalized between 0 and 1. As an example, if a medical source assigns score 70, 85 and 100 to three results, their normalized scores would be 0.333, 0.667 and 1 respectively. For those sources that do not assign a score, a normalized score must be assigned. To assign a normalized score, one is divided by the number of results to determine the lowest score/increment. The lowest result is assigned the lowest score and the next result is assigned the lowest result's score plus the increment. As an example, if a medical source provides five results, 1 divided by 5 is 0.2 so the lowest result is assigned 0.2, next highest is 0.4, next highest is 0.6, and so on.

After each source's results are assigned normalized scores, the normalized score is multiplied by the source weighting multiplier for that medical source. If the user chooses a weighting criteria multiplier of zero, the medical source is not searched. The multiplier may also be adjusted appropriately if for example an end user wishes to give the weighting system of that medical source more or less importance.

Each result has now been assigned a new score (the product of the normalized score and the multiplier). These new scores for all sources are then normalized in aggregate to produce a relevancy ranked list for that tab category.

FIG. 11 shows one embodiment of a preferences screen accessed by preferences link 82 in which a user can pre-select source weighting criteria. Alternatively, this screen can be accessed by selecting the "customize" selection in the user profile section described in more detail below. In the embodiment shown, twelve medical sources including American Family Physician, Care Notes, DynaMed, FP Notebook, Harrisons Online, MDConsult, The Medical letter, Micromedex, and PubMed, are shown with a corresponding numerical search weighting criteria. Google, a popular general web search engine is shown as well because sometimes general world wide web information may be sufficient for a particular user. During searches, results will be ranked not only by their search term matching score, but also according to the weighting criteria selected by the user. The user may select which sources to assign higher weighting criteria to depending on a variety of factors including how well the source is respected, their medical area of focus, and the subject matter of the search performed. Weighting criteria can be adjusted by selecting a numerical value from the drop down menu 96 as shown in FIG. 11 or by other selection methods such as radio buttons or slide bars. When the user has finished adjusting the source weighting criteria, the update button 100 can be clicked to return the user to the search screen or search results screen.

As shown in the screen embodiment of FIG. 12, the user can also select a healthcare profile using the profile selection box 100 to govern the ranking of the search results. Each profile has an associated saved matrix of source ranking criteria selected to best suit that particular healthcare profile. Alternatively, users can select "customize" from the drop down menu and specify the user's own source weighting criteria using an interface such as that shown in FIG. 11.

Additionally, the interface of the current system 60 be configured to provide collaborative tools convenient for those in the medical profession. A user may easily and securely communicate announcements with a specified group such as members of a department, residency program, clerkship, medical school class or clinic. Further, the system 60 allows a user to update a contact list that can be imported and exported to a desktop, a handheld computer, a laptop, or a server. Also, the system 60 can store and allow a user to retrieve request forms or to create evaluation forms and may also allow automated reporting.

The system 60 may further allow a user to keep a calendar of conference schedules, maintain and share call schedules, document resident and student procedures, store links to important web sites, receive email notification of events such as changes to a web site, store personal notes, store department guidelines, store department policies, and store department presentations.

The web site interface 70 is capable of being customized to provide this functionality and is further customized through templates specially tailored to the medical field for more efficient operability.

The system 60 also allows users to provide feedback about the results presented. The system 60 intelligently incorporates these changes to provide better search results for subsequent uses. This can be accomplished by automatically adjusting source weighting criteria after feedback has been provided, or by other relevancy adjustment measures.

In one embodiment, the functionality of the search interface 70 may be built into a handheld computer. Handheld computers will allow a user to use the multitude of annotation or note-taking software programs currently available such as Pocket Word, Pocket Excel, Notes, Documents to Go, Memo Pad, and OneNote and to store and/or synchronize documents created with such software with the system 60. The handheld device may be connected wirelessly to the communications network using technology such as the 802.11 wireless standard or a Bluetooth compatible network.

The search interface is implemented to display found or retrieved documents in a format suitable for viewing on a handheld device. This is accomplished by mining or extracting text and/or removing graphics and frames from web site documents that are not properly formatted. This reformatted text can be browsed or scrolled through on the handheld device.

The system 60 may also be implemented with intelligent search strategies in order to speed the time with which a physician can obtain answers to clinical questions. Some examples may include integrating a medical search engine or thesaurus to provide definitions and correct spelling errors and to find synonyms to medical terms. Terms may be standardized using medical terminology standards from sources such as the National Library of Medicine, the Unified Medical Language System, or a medical dictionary. The system 60 may further be implemented with medical term lists divided into a number of categories. For example, the system 60 may be programmed with a list of drug side effects so that when one of the terms found therein is searched, the drugs with those side effects are retrieved. Also, the system 60 may be programmed to highlight a category most likely to yield the best result for the user, and open the most relevant category for a particular search by default. For example, if a user enters a drug name, then a "drug info" category is highlighted; if a user enters a disease, then a "textbook" category is highlighted.

In another embodiment of the system 60, users use the search interface to manage sharable personal documents. These documents can be related to any of the categories of medical information discussed above. When uploaded or indexed by the system 60, personal documents can be searched by any user using system along with searching other medical sources 24 so long as the user has appropriate user access. In this manner, each user's personal document library becomes another medical source. In an intranet arrangement of users, each user on the intranet has access to each other user's personal documents, without having to have those documents stored to a central server running the search engine. The current system, method, and software product can therefore utilize known peer-to-peer (P2P) document sharing tools, such as the open-source Gnutella file sharing protocol, in conjunction with the search engine to provide this functionality.

Ranking and weighting of medical documents which may be documents retrieved from medical sources or shared personal documents, is also iteratively improved by the system. This is accomplished by recording the frequency of how often a particular document is retrieved by users using the system or user across a particular Intranet. The more often a document is saved, annotated, or otherwise indicated to be of repeated relevance to one or more users, the more ranking weight is given to that document. Actions that can increase a document's weight include but are not limited to saving the document, storing a document as a favorite, linking to the document, referencing the document, and annotating the document.

The system 60 may also be used by a user-physician to retrieve patient education materials. The user-physician may print such materials and distribute them to the user-physician's patients or email them directly to the patient.

Further the system 60 may be programmed to include encryption for the purpose of protecting individually identifiable patient information that my be required for satisfying the requirements of the Health Insurance Portability and Accountability Act of 1996 or HIPAA or for compliance with other regulatory schemes.

The software product of the current method includes a computer readable medium or a downloadable software module with software instructions for programming a computer to performs the tasks and functionality described above written thereon.

While several embodiments of the disclosure is shown and described, it is envisioned that those skilled in the art may devise various modifications and equivalents without departing from the spirit and scope of the disclosure as recited in the following claims.

The invention claimed is:

1. A method for managing medical information on a networked computer system, the method comprising the steps of:

displaying, on a networked computer system, a preferences interface from which a searcher can create a custom profile;

creating, on a networked computer system, a custom profile with source weighting criteria selected by the searcher for a plurality of medical sources identified in the preferences interface;

displaying, on a networked computer system, a search interface for input of a search string, wherein the search interface includes a profile selection portion from which a searcher can select an active profile from a plurality of profiles, including: (1) one or more profiles indicative of healthcare worker types, that include predefined weighting criteria which ranks the plurality of medical sources according to suitability with respective healthcare worker types and (2) the custom profile;

setting, on a networked computer system, the active profile responsive to a selection made by a searcher interacting with the search interface;

performing, on a networked computer system, a real time search using the search string by accessing at least two medical sources to produce a set of search results, the sources being electronically accessible via a communications network;

ranking, on a networked computer system, the set of search results according to the active profile; and displaying, on a networked computer system, the set of search results in a browseable format according to the ranking step.

2. The method of claim 1, further comprising the step of annotating at least one of the search results.

3. The method of claim 1, wherein the real time search also searches personal documents uploaded by a searcher on the networked computer system.

4. The method of claim 3, further comprising the step of providing an interface for inputting metadata about at least one of the search results.

5. The method of claim 3, further comprising the step of providing an interface for inputting metadata about a personal document.

6. The method of claim 5, wherein one or both of a personal document and a search results can be retrieved using a metadata search.

7. The method of claim 6, wherein the metadata is composed of a single keyword.

8. The method of claim 3, further comprising the step of retrieving one or both of a search result and a personal document by browsing through a folder interface.

9. The method of claim 3, further comprising the step of allowing a searcher to assign a user access parameter to a personal document uploaded by the searcher to the networked computer system.

10. The method of claim 3, wherein one or both of a search result and a personal document can be stored as a favorite.

11. The method of claim 1, wherein the communications network is the Internet.

12. The method of claim 1, wherein the step of displaying the search results further includes reformatting the search result to be suitable for viewing on a handheld device.

13. The method of claim 12, wherein reformatting the search results is performed by text extraction of the search result.

14. The method of claim 1, further comprising the step of monitoring actions performed by the user on a search result.

15. The method of claim 14, wherein the action is annotating the document.

16. The method of claim 14, wherein the action is storing the document.

17. The method of claim 14, further comprising the step of improving the relevancy ranking of a search result in response to frequent actions, including indications by one or more users that a particular document is of repeated relevance, being taken by one or more users accessing the set of search results.

18. The method of claim 1, wherein the step of displaying the step of search results is preceded by consolidating multiple search results from a common medical source into a single search result link.

19. The method of claim 1, wherein the source weighting criteria is a numerical value.

20. A computer system comprising:
a preferences interface, on a networked computer system, configured to create a custom profile with source weighting criteria selected by a searcher for a plurality of medical sources identified in the preferences interface;
a search interface, on a networked computer system, configured to input a search string, wherein the search interface includes a profile selection portion from which a searcher can select an active profile from a plurality of profiles, including: (1) one or more profiles indicative of healthcare worker types that include predefined weighting criteria which ranks the plurality of medical sources according to suitability with respective healthcare worker types and (2) the custom profile; and
a search engine, on a networked computer system, configured to perform a real time search using the search string by accessing at least two medical sources electronically accessible via a communications network configured to produce a set of search results and rank the set of search results according to the active profile.

* * * * *